(12) United States Patent
Fan et al.

(10) Patent No.: US 7,982,061 B2
(45) Date of Patent: Jul. 19, 2011

(54) PROCESS FOR PRODUCING EPOXIDES

(75) Inventors: William W. Fan, Lake Jackson, TX (US); Christian D. Kneupper, Brazoria, TX (US); Sascha Noormann, Gruenendeich (DE); Renate Patrascu, Stade (DE)

(73) Assignee: Dow Global Technologies LLC

( * ) Notice: Subject to any disclaimer, the term of this patent is extended or adjusted under 35 U.S.C. 154(b) by 0 days.

(21) Appl. No.: 12/508,435

(22) Filed: Jul. 23, 2009

(65) Prior Publication Data

US 2010/0029958 A1    Feb. 4, 2010

Related U.S. Application Data

(60) Provisional application No. 61/085,747, filed on Aug. 1, 2008.

(51) Int. Cl.
*C07D 301/24*    (2006.01)
(52) U.S. Cl. ........................... 549/521; 549/520
(58) Field of Classification Search ............ 549/520, 549/521
See application file for complete search history.

(56) References Cited

U.S. PATENT DOCUMENTS

| | | | | |
|---|---|---|---|---|
| 2,177,419 A | * | 10/1939 | Engs et al. ............. | 549/521 |
| 4,634,784 A | | 1/1987 | Nagato et al. | |
| 5,532,389 A | | 7/1996 | Trent et al. | |
| 2008/0015370 A1 | | 1/2008 | Hook et al. | |

FOREIGN PATENT DOCUMENTS

| | | |
|---|---|---|
| GB | 2173496 | 10/1986 |
| GB | 2173496 A | 10/1986 |
| JP | 1994-025196 B2 | 10/1991 |
| JP | 6025196 A | 2/1994 |

OTHER PUBLICATIONS

English Patent Abstract of GB 2173496 from esp@cenet, published Oct. 15, 1986, 1 page.
English Patent Abstract of JP 06-025196 from Patent Abstracts of Japan, published Feb. 1, 1994, 2 pages.
Fan, William W. et al, Process for Producing Epoxides, U.S. Appl. No. 12/512,227, filed Jul. 30, 2009, Dow Internal Reference No. 67143-US-NP[1].
Fan, William W. et al, Process for Producing Epoxides, U.S. Appl. No. 12/508,465, filed Jul. 23, 2009, Dow Internal Reference No. 67145-US-NP.

* cited by examiner

*Primary Examiner* — Taylor Victor Oh

(57) ABSTRACT

A process for producing epoxides, the process including: (a) feeding at least one aqueous alkali and at least one halohydrin to a reactive distillation column; (b) concurrently in the reactive distillation column: (i) reacting at least a portion of the halohydrin with the alkali to form an epoxide; and (ii) stripping water and the epoxide from a basic aqueous residue; (c) recovering the water and the epoxide from the reactive distillation column as an overheads fraction; and, (d) condensing and phase separating the overheads fraction at a temperature of 50° C. or less to form an organic overheads fraction including the epoxide and an aqueous overheads fraction including water.

18 Claims, 2 Drawing Sheets

US 7,982,061 B2

PROCESS FOR PRODUCING EPOXIDES

CROSS-REFERENCE TO RELATED APPLICATION

This application, pursuant to 35 U.S.C. §119(e), claims priority to U.S. Provisional Application Ser. No. 61/085,747, filed Aug. 1, 2008, which is hereby incorporated by reference in its entirety.

FIELD OF THE DISCLOSURE

Embodiments disclosed herein relate generally to processes and apparatus to produce epoxides, particularly to processes and apparatus for forming the epoxides via the corresponding halohydrins. More specifically, embodiments disclosed herein relate to dehydrohalogenation processes and apparatus for the continuous production of epoxides by the reaction of the halohydrins with alkali, where the epoxide is distilled from the alkali reaction mixture.

BACKGROUND

Epoxides, including propylene oxide, butylene oxide, epichlorohydrin, and the like are widely used precursors for the production of other compounds. Most epoxides are formed via the halohydrin intermediates and these processes are well known to those skilled in the art, as disclosed in U.S. Pat. No. 5,532,389 and British Patent No. 2,173,496. The halohydrins are most often reacted with an aqueous alkali stream to produce the epoxides and the subsequent halide salt. The epoxide-water azeotrope is advantageously stripped from the aqueous stream to minimize by-product losses from the reaction of water with the epoxide to form glycols such as ethylene glycol, propylene glycol, 3-chloro-1,2-propandiol, glycidol, and glycerine. This overhead product comprising water and epoxide is then condensed and separated in a liquid-liquid phase separator to form an aqueous fraction and an organic fraction containing the crude epoxide, which may be further purified. The aqueous fraction from the overhead is returned to the distillation column as reflux.

In industrial processes, halohydrins are made by reacting low molecular weight olefin-containing compounds, such as propylene, butylene and allyl chloride, with chlorine (or other halogens) and water in a reaction referred to as hypochlorination. The propylene and butylene are converted to chlorohydrins and allyl chloride to dichlorohydrins and subsequently to their respective epoxides (propylene oxide, butylene oxide and epichlorohydrin). This process produces both isomers of the halohydrins and the resulting halohydrins are often dilute in water (<10% by weight) and contain an equivalent of hydrogen chloride (HCl) from the reaction. The halohydrin stream produced by hypochlorination may then be fed directly to a reactive distillation column with an alkali or first, to a pre-reactor for neutralization of the HCl and partial conversion of the halohydrin before introduction into the reactive distillation column. For example, Japanese Patent No. JP1994-025196(B2) discloses a process where dilute dichlorohydrins are mixed with $Ca(OH)_2$ at 40° C. in a pre-reactor and then fed to a 24 plate reactive distillation column where the epoxide (epichlorohydrin) is stripped overhead with water and phase separated from the water in the overhead phase separator to obtain epichlorohydrin in good yields.

Another technology used to a lesser extent in industry is the reaction of glycols with HCl with carboxylic acid catalysis to produce the halohydrins, such as for the production of dichlorohydrins from glycerine as disclosed in U.S. Patent Application No. 20080015370. In this case, mostly one isomer of the halohydrin (1,3-dichlorohydrin) is produced and the remainder of the stream contains less than 30% by weight water and less than 10% HCl by weight. This halohydrin stream is fed with a 10% NaOH stream to a 30 tray reactive distillation column where epichlorohydrin is stripped overhead with water and phase separated from the water in the overhead phase separator to obtain epichlorohydrin in good epichlorohydrin quality.

A third technology used to a lesser extent in industry, specifically for the production of the epoxide, epichlorohydrin, is the catalytic acetoxylation of the propylene into allyl acetate, hydrolysis of the allyl acetate into allyl alcohol, catalytic chlorination of the allyl alcohol into dichlorohydrins as disclosed in U.S. Pat. No. 4,634,784. In this case, mostly one isomer of the halohydrin (2,3-Dichlorohydrin) is produced and the remainder of the stream contains less than 20% by weight water and 5% by weight of HCl. This halohydrin stream is fed with a 9.5% $Ca(OH)_2$ slurry to a column with 10 plates where epichlorohydrin is stripped overhead with water and phase separated from the water in the overhead phase separator to obtain epichlorohydrin in good selectivity.

Epoxides may be produced by the dehydrohalogenation of halohydrins with a base. The halohydrin can be a dilute in aqueous or mostly organic stream and often consists of two isomers as well as HCl. The base is typically an aqueous stream or slurry consisting of NaOH or $Ca(OH)_2$ with or without the presence of a salt, such as but not limited thereby to NaCl and $CaCl_2$. In order to avoid yield losses of the epoxide to hydrolysis, the epoxide is often stripped during the reaction in a distillation column and pH is maintained as close to neutral as possible, as the hydrolysis rate is catalyzed by both acid and base. The glycols produced with some residual organics are not strippable and are lost in the aqueous stream with the salt formed, which exits the bottom of the distillation column and constitute the major yield loss from the dehydrohalogenation process. The bottom aqueous stream may be treated before discharged or recycled. Thus, hydrolysis losses not only impact epoxide yield but also wastewater treatment cost and capital investment.

A wide variety of embodiments of processes and apparatus for the dehydrohalogenation of halohydrins have been proposed in the prior art, however, most have been directed at the by-product hydrolysis losses in the pre-reactor or distillation column. No mention has been made on the by-product hydrolysis losses in the overhead system consisting of the condenser and liquid-liquid phase separator. The aqueous stream from the phase separator is saturated with epoxide, which can still undergo significant hydrolysis at neutral conditions with high temperatures and a poor phase separator design.

Accordingly, there exists a need for improved processes and apparatus for the dehydrohalogenation of halohydrins in which the overall by-product hydrolysis reaction may be reduced in order to obtain good epoxide selectivity and conversion.

SUMMARY OF THE DISCLOSURE

In one aspect, embodiments disclosed herein relate to a process for producing epoxides, the process including: (a) feeding at least one aqueous alkali and at least one halohydrin to a reactive distillation column; (b) concurrently in the reactive distillation column: (i) reacting at least a portion of the halohydrin with the alkali to form an epoxide; and (ii) stripping water and the epoxide from a basic aqueous residue; (c) recovering the water and the epoxide from the reactive distillation column as an overheads fraction; and, (d) condensing and phase separating the overheads fraction at a temperature of 50° C. or less to form an organic overheads fraction including the epoxide and an aqueous overheads fraction including water.

In another aspect, embodiments disclosed herein relate to a process for producing epichlorohydrin, the process including: (a) feeding at least one aqueous alkali and at least one halohydrin comprising at least one of 1,3-dichloropropanol and 2,3-dichloropropanol to a reactive distillation column; (b) concurrently in the distillation column reactor: (i) reacting at least a portion of the dichloropropanol with the alkali to form epichlorohydrin; and (ii) stripping water and the epichlorohydrin from a basic aqueous residue; (c) recovering the water and the epichlorohydrin from the reactive distillation column as an overheads fraction; and, (d) condensing and phase separating the overheads fraction at a temperature of 50° C. or less to form an organic overheads fraction including the epichlorohydrin and an aqueous overheads fraction including water.

Other aspects and advantages will be apparent from the following description and the appended claims.

DETAILED DESCRIPTION

In one aspect, embodiments disclosed herein relate generally to processes and apparatus to produce epoxides, particularly to processes and apparatus for forming epoxides via halohydrins. In a more specific aspect, embodiments disclosed herein relate to dehydrohalogenation processes and apparatus for the continuous production of epoxides by the reaction of halohydrins with alkali, where the epoxide is distilled from the alkali reaction mixture.

As used herein, the term "epoxide" refers to a compound containing oxygen attached to separate saturated carbon atoms, preferably on adjacent carbon atoms. Epoxides, also known as oxiranes, are cyclic ethers and may contain from 2 to about 10 carbon atoms and may be linear, branched, or cyclic. The epoxide may be unsubstituted, but may also be inertly substituted. By "inertly substituted" it is meant that the epoxide is substituted with any group which does not undesirably interfere with formation of the halohydrin or the epoxide. Inert substituents include chlorine, bromine, fluorine, phenyl, and the like. Examples of epoxides may include ethylene oxide, propylene oxide, epichlorohydrin, and butylene oxide, among others.

As used herein, the term "halohydrin" refers to a compound containing at least one hydroxyl group and at least one halogen atom attached to separate saturated carbon atoms, such as adjacent carbon atoms. Halohydrins may contain from 2 to about 10 carbon atoms and may be linear, branched, or cyclic. Halohydrins may be unsubstituted, but may also be inertly substituted. By "inertly substituted" it is meant that the halohydrin is substituted with any group which does not undesirably interfere with formation of the halohydrin or the epoxide. Inert substituents include chlorine, bromine, fluorine, phenyl, and the like. Examples of halohydrins may include bromohydrins and chlorohydrins, such as, but not limited to, 1-chloro-2-ethanol; 1-chloro-2-propanol; 2-chloro-1-propanol; 1,3-dichloro-2-propanol; 2,3-dichloro-1-propanol; 1-chloro-2-butanol; and 2-chloro-1-butanol.

As used herein, the terms "by-product" and "hydrolysis product" refer to a compound produced by the hydrolysis of the epoxide, including derivative compounds from the hydrolyzed compounds. Examples include ethylene glycol, propylene glycol, 3-chloro-1,2-propandiol, glycidol, glycerine, butylenes glycol, and their corresponding ethers.

Figure 1:
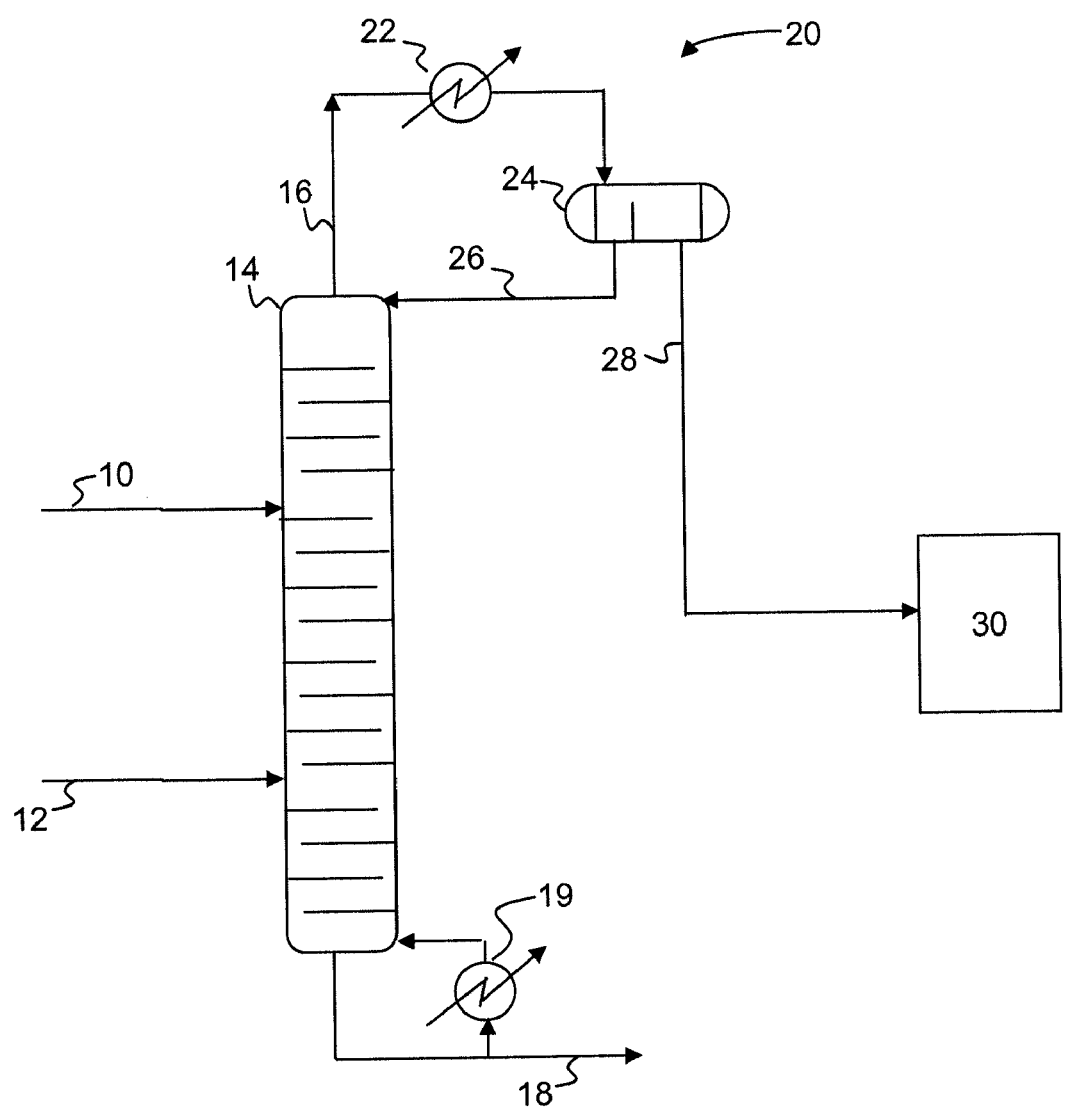
FIG. 1 is a simplified process flow diagram of a process for producing epoxides according to embodiments disclosed herein.

Epoxides may be produced by the dehydrohalogenation of halohydrin with a base, one embodiment of which is illustrated in FIG. 1. At least one aqueous alkali or slurry stream (10) and at least one feed stream comprising halohydrin (12) may be fed to a reactive distillation column (14) to concurrently a) react at least a portion of the halohydrin with the alkali to form an epoxide and b) fractionate water and the epoxide from the basic aqueous residue. The aqueous alkali stream (10) and the halohydrin stream (12) may be fed on different stages or on the same stage. In some embodiments, the aqueous alkali stream (10) is fed above or on the same stage as the halohydrin stream (12). The reactive distillation column (14) may include a plate column, such as perforated-plate column, a tray column, a bubble-cap plate column and/or a packed column and, in some embodiments, has at least 5 theorectical plates.

The water and the epoxide distilled from the reactive distillation column (14) may be recovered as an overheads vapor fraction (16). The basic aqueous residue comprising the halide salt, residual epoxide and halohydrin, and hydrolysis reaction by-products may be recovered from the reactive distillation column (14) as a bottoms fraction (18). A heating or evaporating device, such as a reboiler, may be used for heating or evaporating the liquid in the bottom of the reactive distillation column (14) to provide the vapor driving the separation in the column; alternatively, a stripping agent, such as steam, may be introduced into the bottom of the reactive distillation column (14).

The overheads vapor fraction (16) may then be condensed and phase separated in overheads system (20), which may include a condenser (22) and a liquid-liquid phase separator (24) to form an organic overheads fraction including the epoxide and an aqueous overheads fraction comprising water. The condenser (22) may contain at least one heat exchanger and may either partially or completely condenses or sub-cools the overhead vapor fraction (16). The condenser (22) may be located above the liquid-liquid phase separator (24) so that the condensed liquid phase flows into the liquid-liquid phase separator (24) via gravity flow. The liquid-liquid phase separator (24) may be a device capable of separating fluids according to their relative density such as a decanter.

At least a portion of the aqueous overheads fraction may be returned to the reactive distillation column (14) as reflux via flow line (26). In other embodiments, at least a portion of the aqueous overheads fraction may be treated by another device such as distillation, membrane filtration, and/or adsorption, to remove the epoxide before being return to the reactive distillation column (14) as reflux via flow line (26). The organic overheads fraction, a crude epoxide product stream, may be fed via flow line (28) to an epoxide purification system (30) to purify and recover an epoxide product. At least a portion of the bottom fraction (18) may be biologically or chemically treated or treated using a device, such as distillation, evaporation, membrane filtration and/or adsorption, to remove the residual organics for disposal or recycle to chlor-alkali, lime slaking or hypochlorination processes.

Figure 2:
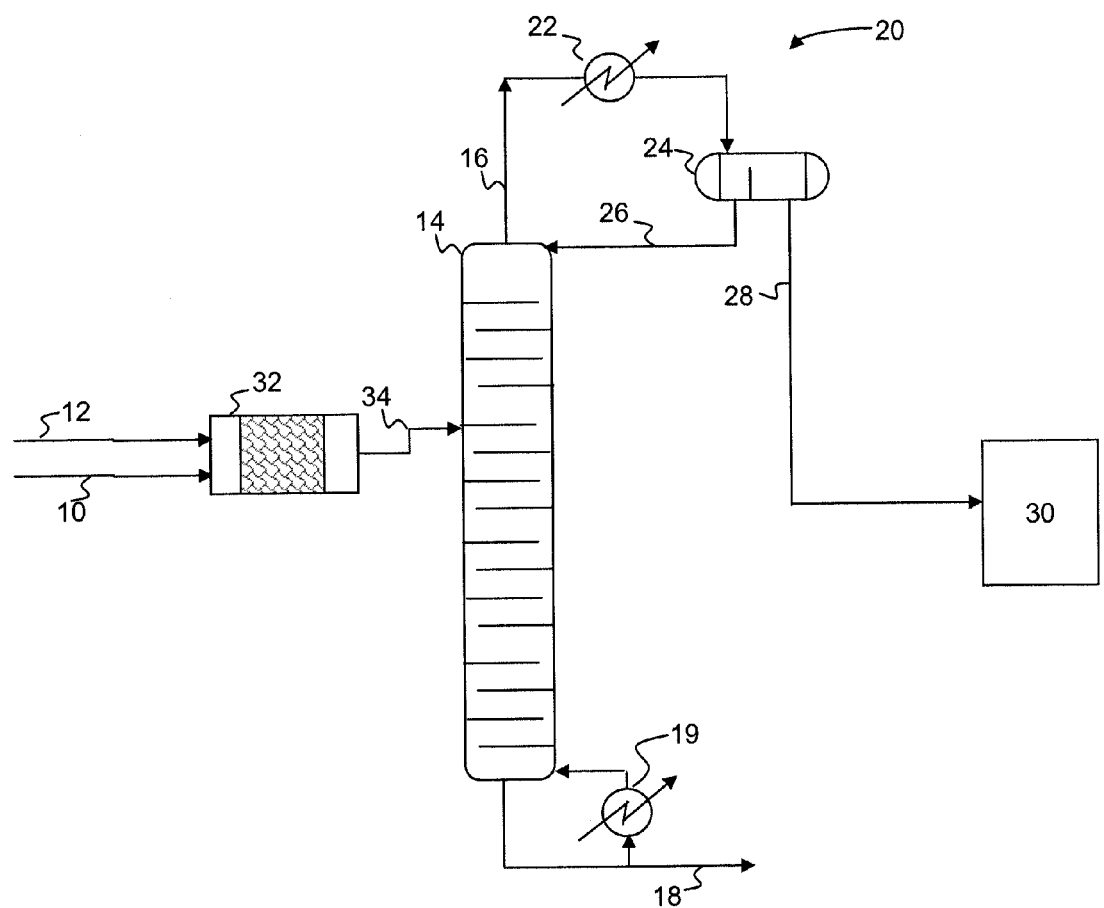
FIG. 2 is a simplified process flow diagram of a process for producing epoxides according to embodiments disclosed herein.

In some embodiments, such as illustrated in FIG. 2, where like numerals represent like parts, at least one feed stream comprising halohydrin (12) may be contacted with at least one aqueous stream including alkali (10) in a reactor (32) to convert at least a portion of the halohydrin to epoxide prior to feeding the hydrocarbon and aqueous base to the reactive distillation column (14) via flow line (34). In some embodiments, the reactor (32) may include a continuous stirred tank reactor (CSTR), a plug flow reactor (PFR), a plug flow mixer/reactor, or any other reactor or combinations useful for the conversion of halohydrins to epoxides.

The condensation and phase separation may be performed, according to embodiments disclosed herein, at a temperature of 50° C. or less to form an organic overheads fraction including the epoxide and an aqueous overheads fraction including water. In other embodiments, the overheads fraction may be condensed and phase separated at a temperature of 40° C. or less; at a temperature of 30° C. or less in other embodiments; at a temperature in the range from 25° C. to 50° C. in other embodiments; and at a temperature in the range from 25° C. to 30° C. in yet other embodiments. The condensation may be performed in at least one heat exchanger, according to embodiments disclosed herein with a suitable coolant. In other embodiments, two heat exchangers may be used, including a first heat exchanger to condense the overhead vapor fraction and a second heat exchanger to sub-cool the condensed liquid stream. The volume of the aqueous side of the liquid-liquid phase separator and the piping for the aqueous reflux back to the reactive distillation column, according to embodiments disclosed herein, should provide a residence time of 60 minutes or less. In other embodiments, the residence time may be 30 minutes or less; and a residence time of 15 minutes or less in other embodiments.

The dehydrohalogenation reaction temperature is not particularly limited; and may be at least 10° C. in some embodiments; at least 30° C. in other embodiments; at least 60° C. in other embodiments; up to 110° C. in other embodiments; up to 100° C. in other embodiments; and up to 90° C. in yet other embodiments. The reaction pressure is not particularly limited, and may range from about 10 millibar to about 1000 millibar. The dehydrohalogenation reaction may be conducted at pressures from about 50 to about 800 millibar in some embodiments; from about 100 to about 500 millibar in other embodiments; and from about 150 to about 400 millibar in yet other embodiments.

In some embodiments, the halohydrin feed stream may include both isomers of the halohydrin. For example, in certain embodiments, the halohydrin feed may include from 0 to 10 percent of the mixture of halohydrins, hydrochloric acid (HCl) in an amount ranging from 0 to about 5 weight percent, and up to about 95 weight percent water. The total halohydrin feed stream may be aqueous and single phase.

In other embodiments, the halohydrin feed stream may include predominately one isomer of the halohydrin. For example, in certain embodiments, the halohydrin feed may include from 55 to 100 percent of the halohydrin, hydrochloric acid (HCl) in an amount ranging from 0 to about 10 weight percent, and up to about 30 weight percent water. The total halohydrin feed may be organic and single phase; or bi-phasic.

The base may include an aqueous alkali metal hydroxide, such as sodium hydroxide, potassium hydroxide, calcium hydroxide, or mixtures thereof. In some embodiments, the aqueous phase may also include an alkali metal salt, such as a sodium halide salt or a calcium halide salt or the like. The amount and concentration of aqueous alkali metal hydroxide is suitably any which results in formation of the corresponding epoxide. The amount of the inorganic base used is not particularly limited. In some embodiments, the amount of the inorganic base used may range from 1.0 to 1.5 times stoichiometric based on moles of halohydrin and any neutralizable chlorinating agent that may be present such as HCl. In other embodiments, the amount of inorganic base used may range from 1.01 to 1.3 times stoichiometric; and from 1.02 to 1.1 times stoichiometric in other embodiments. High concentration of aqueous alkali metal hydroxide may reduce the water loading into the system and the wastewater produced. A concentration of at least about 1% by weight aqueous alkali metal hydroxide may be used in some embodiments; at least about 5% by weight in other embodiments; at least about 10% by weight in other embodiments; and at a concentration within the range from about 10 to about 35% by weight in yet other embodiments.

Dehydrohalogenation according to embodiments disclosed herein may result in a high selectivity to the epoxide, even at high halohydrin conversions. For example, in some embodiments, the dehydrohalogenation may result in a halohydrin conversion of at least 97 mole percent and a selectivity to the epoxide of at least 97 percent; a selectivity of at least 98 percent in other embodiments. In other embodiments, the dehydrohalogenation may result in a halohydrin conversion of at least 98 mole percent and a selectivity to the epoxide of at least 98 percent; and a conversion of at least 99 mole percent at a selectivity of at least 98 percent in yet other embodiments.

EXAMPLES

A dichloropropanol feed (72% 1,3-dichloropropanol, 3% 2,3-dichloropropanol, 5% hydrochloric acid, and 20% water, by weight) is reacted with a 20% sodium hydroxide aqueous solution in a pipe mixer which provides 4 seconds of residence time. The temperatures of the feeds are controlled to achieve a temperature of 60° C. in the mixer. The effluent from the pipe mixer is fed to a distillation column operating at an overhead pressure of 300 millibar. The distillation column consists of 7 trays on top followed by 6.4 meters of packing below. The overhead system consists of a condenser with a decanter to phase separate the organic and aqueous phases. The aqueous phase is refluxed back to the top tray of the column. The feed to the column enters on the $5^{th}$ tray from the top. The column is operated at an aqueous reflux to dichloropropanol feed mass ratio of 1.0 to 1.2. The aqueous reflux has a residence time of 1 hour in the overhead system before being returned back to the column. Different condenser temperatures are used in the experimental runs, as shown in Table 1. Conversion is calculated as 1 minus the ratio of the dichloropropanols in the organic stream from the decanter and the dichloropropanol feed. Yield loss is calculated from the moles of total organic leaving the bottom of the distillation column from the moles of dichloropropanols that is converted. Results are presented in Table 1.

TABLE 1

| Experiment | Condenser Temperature (° C.) | Conversion (%) | Yield Loss (%) |
|---|---|---|---|
| 1 | 45 | 99 | 1.7 |
| 2 | 41 | 99 | 1.3 |
| 3 | 38 | 99 | 1.2 |
| 4 | 33 | 99 | 1.0 |
| 5 | 29 | 99 | 0.9 |

It has been found that significant hydrolysis of the epoxide can still occur in the overhead system of the distillation column. After phase separation in the decanter, the aqueous stream is saturated with the epoxide and depending on the decanter design and equipment layout, the residence time to reflux this aqueous stream could be substantial. In addition, cooling medium in industry for the condenser is typically cooling tower water, therefore, decanter temperatures of greater than 50° C. are common, and coupled with the high residence time of the overhead system, may lead to significant hydrolysis of the saturated amount of epoxide in the aqueous stream, even at near neutral pH. Lowering the condensation and phase separation temperature to a temperature of 50° C. or less, as described above, may reduce epoxide hydrolysis and improve product yield. The use of lower temperatures reduces both the hydrolysis reaction rate and the solubility of epoxide in the aqueous phase allowing for a better phase separation, thus resulting in a decrease in hydrolysis and an improved yield. In addition, residence time for the aqueous phase in the decanter and the aqueous reflux piping should be minimized as much as possible.

As described above, embodiments disclosed herein may provide for reaction of halohydrins with a base to form epoxides at a high selectivity (such as ≧ about 97 percent) and a high yield (such as ≧ about 97 percent). For example, embodiments disclosed herein may advantageously decrease epoxide hydrolysis in the overhead system of a reactive distillation column used for the conversion of the halohydrin to the corresponding epoxide, as compared to conventional recovery systems. The decreased hydrolysis may be attained by maintaining the overheads condenser temperature at about 50° C. or less, for example, resulting in a decrease in both the hydrolysis reaction rate and the solubility of the epoxide in water.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A process for producing epoxides, the process comprising:
   (a) feeding at least one aqueous alkali and at least one halohydrin to a reactive distillation column;
   (b) concurrently in the reactive distillation column:
      (i) reacting at least a portion of the halohydrin with the alkali to form an epoxide; and
      (ii) stripping water and the epoxide from a basic aqueous residue;
   (c) recovering the water and the epoxide from the reactive distillation column as an overheads fraction;
   (d) condensing and phase separating the overheads fraction at a temperature of 50° C. or less to form an organic overheads fraction comprising the epoxide and an aqueous overheads fraction comprising water; wherein a residence time for the aqueous overheads fraction in the overhead system is 1 hour or less.

2. The process of claim 1, wherein the condensing and phase separating is performed at a temperature of 30° C. or less.

3. The process of claim 1, further comprising feeding at least a portion of the aqueous overheads fraction to the distillation column reactor as reflux.

4. The process of claim 1, further comprising feeding at least a portion of the organic overheads fraction to an epoxide purification system.

5. The process of claim 1, further comprising contacting the halohydrin and the aqueous alkali in a reactor to convert at least a portion of the halohydrin to epoxide prior to the feeding.

6. The process of claim 1, wherein the halohydrin comprises at least one of 1-chloro-2-ethanol; 1-chloro-2-propanol; 2-chloro-1-propanol; 1,3-dichloro-2-propanol; 2,3-dichloro-1-propanol; 1-chloro-2-butanol; and 2-chloro-1-butanol.

7. The process of claim 1, wherein the aqueous alkali comprises at least one of sodium hydroxide and calcium hydroxide.

8. The process of claim 7, wherein the aqueous alkali further comprises at least one of a sodium halide salt and a calcium halide salt.

9. The process of claim 1, wherein a halohydrin conversion is at least 98 mole percent, and wherein a selectivity to the epoxide is at least 98%.

10. A process for producing epichlorohydrin, the process comprising:
    (a) feeding at least one aqueous alkali and at least one halohydrin comprising at least one of 1,3-dichloropropanol and 2,3-dichloropropanol to a reactive distillation column;
    (b) concurrently in the distillation column reactor:
       (i) reacting at least a portion of the dichloropropanol with the alkali to form epichlorohydrin; and
       (ii) stripping water and the epichlorohydrin from a basic aqueous residue;
    (c) recovering the water and the epichlorohydrin from the reactive distillation column as an overheads fraction; and
    (d) condensing and phase separating the overheads fraction at a temperature of 50° C. or less to form an organic overheads fraction comprising the epichlorohydrin and an aqueous overheads fraction comprising water; wherein a residence time for the aqueous overheads fraction in the overhead system is 1 hour or less.

11. The process of claim 10, wherein the condensing and phase separating is performed at a temperature of 30° C. or less.

12. The process of claim 10, wherein a residence time for the aqueous overheads fraction in the overhead system is 0.5 hour or less.

13. The process of claim 10, further comprising feeding at least a portion of the aqueous overheads fraction to the distillation column reactor as reflux.

14. The process of claim 10, further comprising feeding at least a portion of the organic overheads fraction to an epichlorohydrin purification system.

15. The process of claim 10, further comprising contacting the dichloropropanol and the aqueous alkali in a reactor to convert at least a portion of the dichloropropanol to epichlorohydrin prior to the feeding.

16. The process of claim 10, wherein the aqueous alkali comprises at least one of sodium hydroxide and calcium hydroxide.

17. The process of claims 16, wherein the aqueous alkali further comprises at least one of a sodium halide salt and a calcium halide salt.

18. The process of claim 10, wherein the dichloropropanol conversion is at least 98 mole percent, and wherein the selectivity to epichlorohydrin is at least 98 mole percent.

* * * * *